United States Patent [19]

Ainsworth et al.

[11] Patent Number: 4,892,552
[45] Date of Patent: Jan. 9, 1990

[54] ORTHOPEDIC DEVICE

[76] Inventors: Robert D. Ainsworth, 118 Castle Hill Ranch Rd., Walnut Creek, Calif. 94595; Thirumalai N. C. Devanathan, 1801 Duncan, Tracy, Calif. 95576; Steven T. C. Lin, 7100 San Ramon Rd., Dublin, Calif. 94566

[21] Appl. No.: 904,592

[22] Filed: Sep. 8, 1986

Related U.S. Application Data

[63] Continuation of Ser. No. 595,215, Mar. 30, 1984, abandoned.

[51] Int. Cl.$^4$ ............................ A61F 2/32; A61F 2/30
[52] U.S. Cl. .......................................... 623/23; 623/16; 623/66; 623/901
[58] Field of Search ................... 428/902, 113; 623/16, 623/20, 21, 22, 23

[56] References Cited

U.S. PATENT DOCUMENTS

| | | | |
|---|---|---|---|
| 3,556,922 | 1/1971 | Green et al. | 428/902 |
| 3,707,006 | 12/1972 | Bokros et al. | 623/16 |
| 3,893,196 | 7/1975 | Hochman | 623/16 |
| 4,089,071 | 5/1978 | Kalnberz et al. | 623/16 |
| 4,157,181 | 6/1979 | Cecka | 428/902 |
| 4,221,623 | 9/1980 | Heissler et al. | 623/18 |
| 4,329,743 | 5/1982 | Alexander et al. | 623/16 |
| 4,356,571 | 11/1982 | Esper et al. | 623/22 |
| 4,459,708 | 7/1984 | Buttazzoni | 623/18 |

Primary Examiner—Richard J. Apley
Assistant Examiner—David J. Isabella

[57] ABSTRACT

An orthopedic device formed from a composite material which is reinforced with continuous filament carbon fibers to provide the material with high flexural strength, hydrolytic stability and a medical grade quality. A preferred embodiment of the orthopedic device is a hip joint prosthesis in which the stem and spherical head of the prosthesis can be formed from a composite block. In the alternative, the stem alone can be formed from the block and a head of another material attached to one end of the stem. One embodiment of the method includes first forming a sheet of carbon fibers by wrapping carbon fiber tows spirally around a drum after passing the tows through a thermoplastic resin which serves as a bonding agent. Then, rectangular pieces of the carbon fiber-polymer sheet are combined one with another to form a stack. Pressure is exerted on the stack in the presence of heat to form the composite block. Following the formation of the block, the block is machined to form the desired orthopedic device. In another embodiment of the method, sheets of carbon fibers held together by a polymer are rolled into a cylinder, then molded under heat and pressure. The resulting composite is then machined to form the orthopedic device.

11 Claims, 2 Drawing Sheets

ORTHOPEDIC DEVICE

This is a continuation of application Ser. No. 595,215 filed Mar. 30, 1984 now abandoned.

FIELD OF THE INVENTION

The present invention relates to orthopedic devices implanted in the body, and more particularly, to a load bearing orthopedic device and a method for making such a device from a composite material.

BACKGROUND OF THE INVENTION

Metallic orthopedic devices, though extensively used, exhibit problems that are inherent due to the high modulus of the metals used in the devices. A majority of the total joint replacement orthopedic devices implanted to date are of the type comprised of a metallic surface bearing on an ultra-high molecular weight polyethylene cup surface. For hip replacement, for instance, there is a metallic femoral component consisting of a highly polished spherical head attached to a narrow neck which then widens to a tapered shaft design to conform to the contours and to be inserted into the medullary canal. The metal of the shaft is usually a cobalt-chromium-molybdenum alloy or a titanium alloy with mechanical properties and load bearing ability far in excess of that of the bone itself. In a majority of cases, the shaft is attached to the bone by bone cement (e.g., poly methyl methacrylate) which has been packed into the cavity after oversize reaming. The implant shaft is then forced into the curing bone cement and attachment is primarily due to mechanical interlocking.

Failure of hip devices have occurred in many patients. Multiple fractures in the bone cement can lead to the loosening of the implant and the eventual fatigue fracture of the shaft or stem of such a device in vivo. Most important factors contributing to this failure are the design of the stem, the quality and thickness of the bone cement, surgical techniques of bone preparation and cement insertion, imperfections such as metal defects and voids, and improper stress transfer through the surrounding bone by the stem.

One reason for failure of the devices is that resorption of the bone surrounding the proximal portion of the implant stem can lead to cement failure, resulting in the loosening of the stem in the bone. A loose stem cannot function properly and can cause the implant to fail even if the stem itself has not fractured. It is expected that a lower modulus stem will lead to a greater transfer of stresses to the bone in the calcar region and prevent or lessen the degree of resorption of the bone in this region. Based upon this concept, titanium alloy hips have been introduced by several orthopedic manufacturers since it has approximately half of the elastic modulus of cobalt-based alloys. It has been found that reducing stem modulus increases the transfer of load from the stem to the bone. This lack of "stress shielding" effect will lead to a reduction in bone resorption.

Bio-compatible composite materials have been determined to offer the unique advantage of being light weight in construction and high in strength at low modulus values. By far, the most popular composite material for orthopedic implants is one in which reinforcing is due to carbon fibers. A hip prosthesis has been made in the past in which the stem is formed of carbon fiber reinforced carbon and a spherical head is made of aluminum oxide.

Other attempts have been made to investigate the mechanical behavior of fiber reinforced materials specifically for prothesis of different types. Various polymers in combination with carbon or glass fibers were considered in the studies. For instance, it has been shown that quartz and graphite fiber reinforced epoxy composite with strength in the vicinity of 1400 Mpa could be made and proven to be acceptable for implant service. (Musikant, "Quartz and Graphite Filament Reinforced Polymer Composites for Orthopedic Surgical Applications," *J. Biomed. Mater. Res. Symp.*, Vol. 1, pp. 225-235, 1971). In another publication, reports were made of mechanical properties in vitro of a low modulus epoxy carbon fiber composite. (Bradley et al., "Carbon Fiber Reinforced Epoxy as a High Strength Low Modulus Material for Internal Fixation Plates," *Biomaterials*, Vol. 1, January, 1980). Composite plates were made suitable for internal fixation of fractures. The plates showed superior flexural strength and fatigue properties in comparison with stainless steel plates while having approximately one third the stiffness.

In another publication, namely Litchman et al., "Graphite Reinforced Bone Cement Practical in Orthopedic Surgery", *Orthopedic Review*, Vol. X, No. 3, March, 1981, a report is made of a 64% increase in strength and a 200% increase in the stiffness of poly methyl methacrylate bone cement due to the addition of just 3% by weight of carbon fiber. While this article suggests such a composite to be of great value as a load bearing implant, other researches have found it to be unsuitable.

Still another publication mentions the use of a carbon fiber-polysulfone composite for making surgical implants but does not specify how the composite is made. This publication is by M. S. Hunt, entitled, "ME1689 An Introduction to the Use of Carbon Fiber Reinforced Composite Materials for Surgical Implants" National Mechanical Engineering Research Institute, Counsel for Scientific and Industrial Research, January 1981, Series No. MEI/8, Reference No. MEI/4054 (Pretoria).

In the present invention, there is disclosed a carbon fiber reinforced polymer composite specifically for use in load bearing orthopedic implants, such as hip joints, knee joints, bone plates and intramedullary rods.

SUMMARY OF THE INVENTION

The orthopedic device of the present invention is formed from a composite material comprised of continuous filament carbon fibers embedded within a polymer matrix. The carbon fibers in the composite material are at specific orientations relative to a specific dimension of the orthopedic device. Maximum tension and compression strength is achieved when the orientation of the fibers extend longitudinally of the orthopedic device, such as the stem of a hip prothesis. However, torsional and shear strength of the device suffers when the fibers extend parallel to the longitudinal axis. In the case of a hip prothesis which has an upper part which projects upwardly and outwardly from the stem of the prothesis, the strength of the upper projecting part must also be considered and, for this reason, some of the carbon fibers are made to extend longitudinally of the stem and other carbon fibers at an angle to the longitudinal axis of the stem. The angularity of the angled carbon fibers is made on a basis of the design of the prothesis itself. By changing the angularity of the carbon fibers at various levels in the composite, optimum strength in all critical load directions in light of the function of the orthopedic device can be provided.

By using the materials of the present invention, one can engineer a structure to meet a particular need. Thus, modulus of elasticity can be varied within ranges to more closely approximate that of the bone in the region where the implant is to function. In addition, based on the type of loading, modulus can be varied along the longitudinal axis of the device as well as torsional strength. These fiber/resin composite materials provide an advantage over metals which by necessity are homogeneous in nature and cannot provide this engineering flexibility. Thus, with metal implants, variation of tensile strength and modulus for a given metal is not possible.

The modulus of bone is generally about 3 msi. The modulus of currently available titanium implants is approximately 16 msi. Stainless steel and cobalt chrome, also commonly available, have moduli of 32 msi or more. As previously stated, by reducing stem modulus and transferring the load from the stem to the bone, this leads to a reduction in bone resorption. The closer the modulus of the implant to that of bone, the less the stress shielding. With the implants of the present invention, by proper design, moduli of between 9 msi and 10 msi are easily obtained, while maintaining sufficient tensile strength to permit the use of the composite as a supporting structure.

At the same time as modulus is being reduced, tensile strength of the device is to be optimized. This may be most easily accomplished by adjusting the content of the fiber volume relative to that of the bio-compatible thermoplastic polymer. A minimum of about 30% polymer is required in order to form the matrix.

With the device, starting with a maximum of approximately 70% fiber, 30% resin, one can reduce fiber content and increase polymer content to decrease modulus. However, there is an attended reduction in tensile strength. Thus, while one could continue to reduce the fiber content, a point would be reached where tensile strength could be reduced to the point the device would no longer be functional.

We have found that further modulus reductions can be obtained while at the same time maximizing tensile strength by varying the angle of the fibers within the composite. Thus, instead of adding polymer to reduce modulus with the attended undesirable decrease in tensile strength, we are able to achieve an implant of suitable properties by varying fiber orientation. We have found generally that the fiber content should not exceed 70%, and preferably is between 40 and 60%. The precise ratio of polymer to fiber and orientation of fibers within the various layers will be a function of design device.

By laboratory testing, the strength and modulus of elasticity of a carbon fiber reinforced polysulfone composite is demonstrated to change substantially when the fiber orientation is at different angles to the load angles of the test. Table 1 illustrates this point.

TABLE 1

| Effect of Fiber Orientation on the Strength and Modulus of Elasticity of 66 wgt % CF/34 wgt % PS Composite | | |
|---|---|---|
| Fiber Orientation | Tensile Strength (ksi) | Tensile Modulus (msi) |
| 0° | 264.00 | 18.00 |
| ±15° | 90.00 | 9.00 |
| ±45° | 28.03 | 1.82 |

TABLE 1-continued

| Effect of Fiber Orientation on the Strength and Modulus of Elasticity of 66 wgt % CF/34 wgt % PS Composite | | |
|---|---|---|
| Fiber Orientation | Tensile Strength (ksi) | Tensile Modulus (msi) |
| 90° | 7.65 | 1.18 |

The mechanical properties of the composite can also be modified by varying the ratio of polymer to carbon fiber within the composite material. The uniaxial tensile strength and modulus of elasticity of carbon fiber alone is 450 ksi and 33 msi, respectively. Polysulfone, a representative engineering thermoplastic, has a tensile strength of approximately 10 ksi and a modulus of elasticity of 360 ksi. When these materials are combined into a composite, a wide variation in mechanical properties can be achieved at different fiber to polymer ratios. Table 2 presents mechanical properties measured for composites which range from 50% to 60% by weight of carbon fiber.

TABLE 2

| Effect of Polymer Content on the Strength and Modulus of Elasticity of Unidirectional Carbon Fiber/ Polysulfone Composites. | | |
|---|---|---|
| Fiber Weight (%) | Tensile Strength (ksi) | Tensile Modulus Of Elasticity (msi) |
| 50 | 179 | 15 |
| 55 | 186 | 17.3 |
| 60 | 194 | 19.5 |

From: Hogatt, J.T., "Study of Graphite Fiber Reinforced Thermoplastic Composites," Boeing Aerospace Company, NTIS AD-778-000

It can be seen from the above data that, when designing a composite material structure for a particular orthopedic device design, the properties of this composite can be optimized to the requirements of the particular device design by varying fiber orientation and fiber to polymer ratio.

The object of the present invention involves a composite of carbon fiber reinforced engineering thermoplastic polymer. Polysulfone has been studied as a candidate engineering thermoplastic matrix polymer and many of the mechanical properties presented above are for this carbon fiber/polysulfone composite. Polysulfone has been used extensively as a medical device material and its biocompatibility and toxicity properties have been well characterized. As such, it is an excellent polymer for combination with carbon fiber as presented by this disclosure.

Engineering thermoplastics include many polymers and a number of them in addition to polysulfone have been investigated as part of this invention. Engineering thermoplastics can be defined as a class of thermoplastic resins which exhibit high ultimate tensile strength, rigidity, creep resistance, and toughness, and include, but are not limited to, the following polymers: polysulfone; polyethersulfone; polyarylsulfone; polyphenylene sulfide; polycarbonates; aromatic polyamides; aromatic polyamideimides; thermoplastic polyimides, and the polyaryletherketone polyetheretherketones; polyarylethernitriles; aromatic polyhydroxyethers; and the like.

Typical mechanical properties for an engineering thermoplastic are an ultimate tensile strength of 10,000 psi, an elastic modulus of 250,000–500,000, psi, and an elongation to break of from 10% to 100%. Composites of carbon fibers and several of these polymers have been made, including polyether sulfones of three different molecular weights (ICI 200 p, ICI 300 p, and ICI 720 p), polyaryl sulfone (3M Company Astrell), polyimide (DuPont NR150-A) and polyimide-amide (Amoco Torlon 4000). Typical mechanical properties of these polymers are presented in Table 3.

TABLE 3

Mechanical Properties of Carbon Fiber Reinforced Engineering Thermoplastic Composites.

| Composite | Unidirectional Sheet | | Unidirectional Sheet | |
|---|---|---|---|---|
| | Flexural Strength (ksi) | Flexural Modulus (msi) | Interlaminar Shear (psi) | Fiber Volume (%) |
| CF/PES (ICI 720 p) | 163 | 12.2 | 10.5 | 60 |
| CF/PES (ICI 200 p) | 189.9 | 14.4 | 12.2 | 60 |
| CF/PES (ICI 300 p) | 189.7 | 12.7 | 12.4 | 56 |
| CF/PAS (3 M Astrel 360) | 121.9 | 10.7 | 6.7 | 60 |
| CF/Polyimide (NR-150A; DuPont) | 159 | 12.1 | 12.2 | 55 |
| CF/Polyimide-amide (Torlon 4000; Amoco) | 140.8 | 13.1 | 6.2 | 55 |

CF: carbon fiber; PES: polyethersulfone; PAS: polyarylsulfone.
From: Hogatt, J. T. and Von Volkli, A.D., "Evaluation of Reinforced Thermoplastic Composites and Adhesives," Boeing Aerospace Company, NTIS AD/A-01140

The mechanical properties of these composite materials are comparable to structural metal alloys that are presently used to manufacture orthopedic devices. The maximum values for composite properties are measured along the axis of the fiber orientation. Tensile strength and modulus of elasticity values for a unidirectional carbon fiber/polysulfone composite are presented in comparison to common orthopedic alloys in Table 4.

TABLE 4

Tensile Strength and Modulus of Unidirectional CF/PS Composite and Conventional Orthopedic Alloys.

| Material | Tensile Strength (ksi) | Tensile Modulus Of Elasticity (msi) |
|---|---|---|
| Carbon Fibers | 405 | 33 |
| CF/PS (57% fiber vol.) | 264 | 18 |
| Ti—6AL—4V (forged) | 125 | 16 |
| 316 Stainless Steel (forged) | 110 | 32 |
| Co—Cr—Mo (CAST) | 90 | 32 |
| CF/PF (52% fiber at ±15° fiber orientation) | 90 | 9 |

The building material for the devices of this invention are uniplanar sheets of continuous filament carbon fiber tows encapsulated in the engineering thermoplastic polymer matrix, the fibers being arranged in parallel within the uniplanar sheet and are continuous within the sheet. The fiber tows are comprised of bundles of filaments, commercially available tows having approximately 5,000–15,000 filaments/bundle. There is no preferred filament diameter. However, for reasons of availability and manufacturing suitability, it is preferable to use such materials as those provided by Hercules under the designation Hercules AS4, containing approximately 12,000 fiber filaments/tow, each filament having a diameter of approximately 7–9 microns. The uniplanar sheets are formed using continuous filament fiber.

To effect fiber orientation, these uniplanar sheets are first formed and then cut into coupons and stacked to form blocks or they can be rolled upon themselves to form cylinders from which the final device can be fashioned. The manner in which the sheets or coupons are oriented will effect final modulus and tensile properties. In addition, torsional strength can be effected with the rolled sheet device having higher torsional strengths, especially if in the rolling process, the sheet is rolled off axis. Such technique will impart a spiraling of the fibers along the longitudinal axis of the device.

By way of example, in one embodiment for making the orthopedic device of the present invention, in a series of steps in which the composite block is formed, a block is formed from a multiplicity of stacked coupons comprised of a plurality of carbon fibers and a polymer, such as polysulfone. The block is typically rectangular in shape and of a predetermined thickness, such as 0.5 inch. to 1.25 inches. The block is machined to the desired shape of the orthopedic device and, after smoothing its outer surfaces, the device is ready for use as an implant.

In the case of a hip prosthesis, the stem and head of the prosthesis can be integral with each other and formed simultaneously from the composite block. In the alternative, the stem can be formed from the block and a head of metal can then be attached to one end of the stem to form the prosthesis.

The composite block used to form the prosthesis has polymer in the range of 25 to 50% by weight, and preferably 30–40%, the carbon fiber content making up the remainder of the block.

The primary object of the present invention is to provide an improved orthopedic device and method of making the same wherein the device is comprised of a continuous filament carbon fiber reinforced polymer. In one embodiment, it is formed by laminating a stack of carbon fiber pieces under heat and pressure to form a composite block and the block is machined to the desired shape and size of the orthopedic device, whereupon the device has optimized mechanical properties for the orthopedic device and is of medical grade quality. In a second embodiment, at least one uniplanar sheet is rolled upon itself to form a cylinder from which the final shape is obtained.

Other objects of this invention will become apparent as the following specification progresses, reference being had to the accompanying drawing which shows schematic views of the steps in the formation of the orthopedic device.

IN THE DRAWINGS

Figure 1:
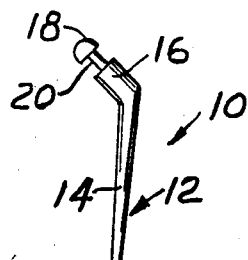
FIG. 1 is a side elevational view of a hip prosthesis which is formed from the method of the present invention.
Figure 2:
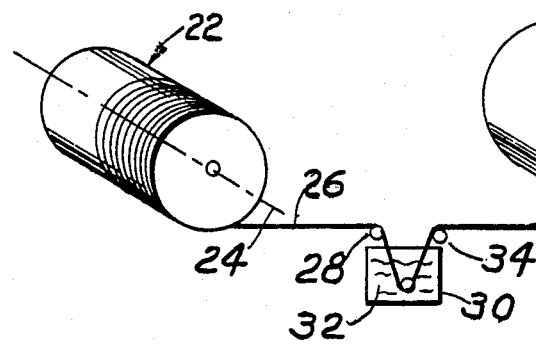
FIG. 2 is a schematic view showing the way in which a laminate of carbon fibers is made, the laminate being used to form a composite block from which the prosthesis of FIG. 1 is formed.

To illustrate the first embodiment of the present invention, reference is made to FIG. 1 which shows a hip prosthesis 10 having a stem 12 provided with a lower main shaft 14 and an upper, inclined neck or extension 16. A femoral head 18 which is generally spherical in configuration is attached by a short neck 20 to extension 16. The various parts of prosthesis 10 are all integral with each other and are formed from a composite block made with carbon fibers and polysulfone in the manner hereinafter described In carrying out the teachings of the present invention, a roll 22 (FIG. 2) of carbon fiber tow 26 is mounted for rotation on any suitable support for rotation about a generally horizontal axis 24.

The tow 26 is passed over a first guide 28, then into a vessel 30 containing a solution 32 of a suitable polymer, such as polysulfone in methylene chloride or other suitable solvent. Any one of the other above-mentioned polymers may be used. Polysulfone will hereinafter be referred to as the polymer.

The tow is thus coated with the polysulfone and as the tow leaves the vessel 30, it is directed by guide 34 toward and about a rotating drum 38 on which the polysulfone-coated tow is wrapped spirally to form side-by-side convolutions which engage each other. The spiral wrap of the tow on the drum is for the purpose of forming a laminate 40 of carbon fibers.

Figure 3:
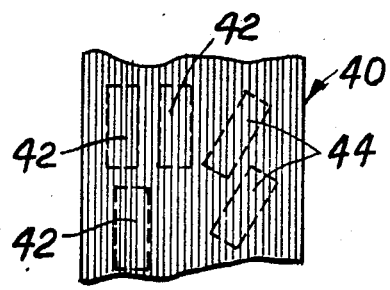
FIG. 3 is a plan view of a portion of the carbon fiber laminate taken from the drum of FIG. 2.

After the polysulfone has dried on the drum, the resulting sheet represents the laminate 40 which can be cut into pieces of rectangular shape. Laminate 40 is comprised of adjacent, side-by-side, strips of carbon fibers. In this form, the laminate is cut into rectangular pieces or "coupons" which are shown in dashed in lines in FIG. 3. Coupons 42 are shown in which longitudinal axes of the coupons are parallel to the carbon fibers in the coupons. Coupons 44 are cut from laminate 40 and have their carbon fibers at an angle with respect to the longitudinal axes of the coupons 44. The reason for this will be set forth hereinafter The cutting of the coupons 42 and 44 can be accomplished by a stamping process or other suitable technique.

Figure 4:
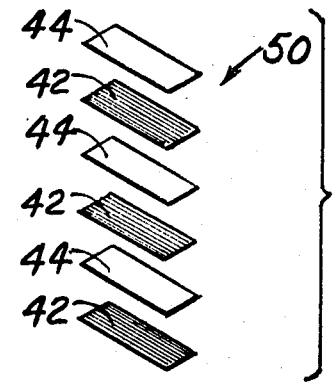
FIG. 4 shows a stack of pieces of carbon fiber laminate of FIG. 3.
Figure 5:
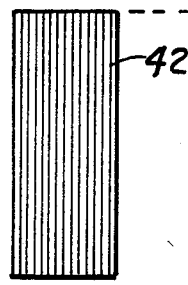
FIG. 5 is a plan view of one of the coupons of carbon fiber laminate showing the carbon fibers extending parallel to the longitudinal axis of the coupon.
Figure 6:
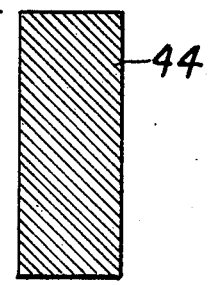
FIG. 6 is a view similar to FIG. 5 but showing the carbon fibers at an angle with respect to the longitudinal axis of the piece.
Figure 7:
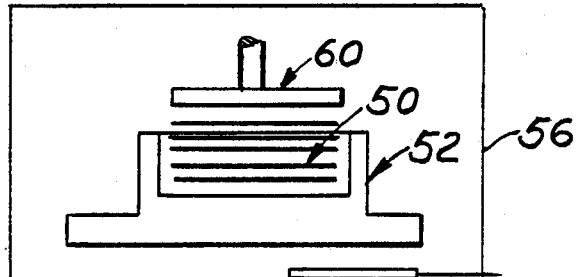
FIG. 7 is a schematic view of a heated mold mounted in a press, the mold containing the stack of pieces shown in FIG. 6.
Figure 8:
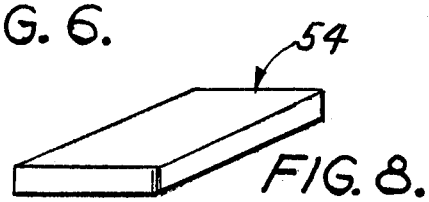
FIG. 8 is a prospective view of the composite block formed from the application of heat and pressure to the stack in the mold of FIG. 7.

Coupons 42 and 44 are arranged in a stack 50 (FIG. 4) so that they can be placed in a mold 52 (FIG. 7) and, while under heat and pressure in the mold, the polysulfone in the stack will melt and flow to form a composite block 54 (FIG. 8) from which the prosthesis 10 can be machined. Moreover, the carbon fiber coupons 42 will alternate with the carbon fiber coupons 44 as shown in FIG. 4. When stack 50 is formed, it will be placed in mold 52 having heating elements 58 therein. A press 60 is adapted to apply pressure in the range of 800 to 1200 psi to the stack 50 in mold 52. The temperature of the mold will be in the range of 500° to 700° F. as pressure is applied by press 60 to the stack 50.

Figure 9:
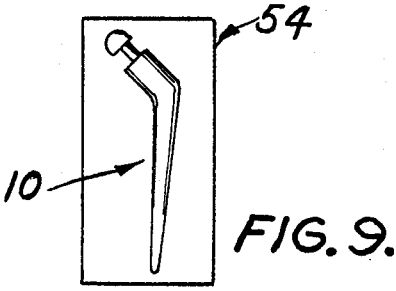
FIG. 9 shows the design of the prosthesis of FIG. 1 in the block of FIG. 8, the block being machined to form the prosthesis.

Following a molding time, typically one hour or more, and after a cooling period, the block 54 will be formed in mold 52. Then, the block is taken from the mold and then machined by suitable tools to form prosthesis 10. The prosthesis is outlined in FIG. 9 in block 54 and, in this case, head 18 is formed as an integral part of stem 12. In final preparation for use, the head is typically provided with a coating to harden the surface thereof. In the alternative, only stem 12 is formed from block 54, and a metallic head is secured to the stem in any suitable manner, such as with an epoxy adhesive.

The orientation of fibers in a particular implant design can be chosen to optimize mechanical properties for that design. For example, in a hip implant design in which the neck 16 of the prosthesis is at an angle of 45° to the stem 14 of the prosthesis (FIG. 1), a combination of laminates for the block could be chosen as follows: 70% at 0° and 30% at ±45°; or 60% at 0°, 30% at ±15°, and 10% at 90° fiber orientation to provide sufficient strength in the stem and neck of the design. The modulus of elasticity also changes as various fiber orientations of the laminates are used so that a modulus could be chosen for each specific design.

Figure 10:
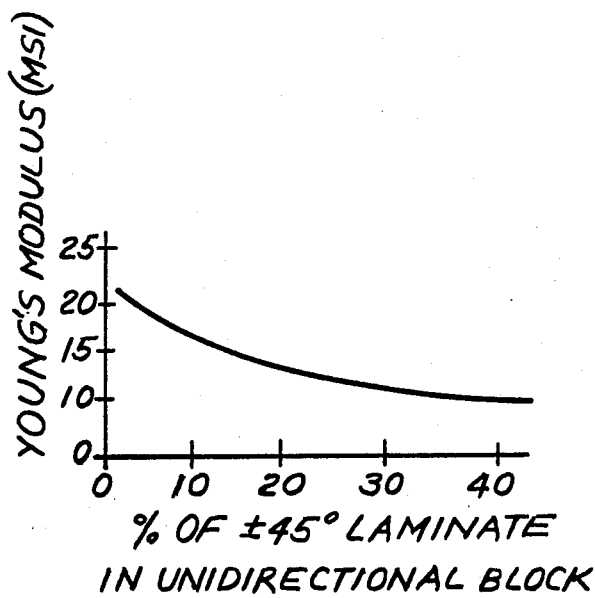
FIGS. 10 and 11 are graphic views of mechanical properties of the composite material with various fiber angles.
Figure 11:
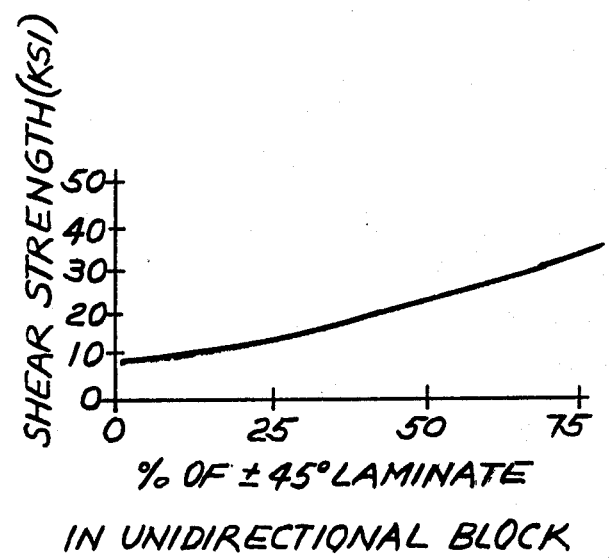

The graphs in FIGS. 10 and 11 demonstrate how mechanical properties can change as the percentage of ±45° laminates used in a composite block increases, the data shown for a fiber-resin ratio of 60–40.

A second method of producing a composite orthopedic device from these same materials is as follows:

1. Carbon fiber tow is solution-coated with polymer and then allowed to dry on a mandrel, similar to that described previously. The result is a two-dimensional sheet of parallel carbon fibers held together by the dried polymer matrix;
2. From this sheet is cut patterns of specific shape and fiber orientations;
3. These patterns are then tightly rolled into a cylinder;
4. The roll is then placed into a suitable mold and under heat and pressure, the polymer in the rolled sheets melts and flows and upon cooling, consolidated dates the cylinder into a dense composite.

Figure 12:
FIGS. 12–15 are schematic views showing different patterns for use in making an implant.
Figure 13:
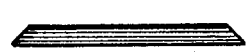
Figure 14:
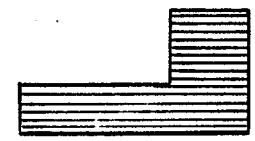
Figure 15:
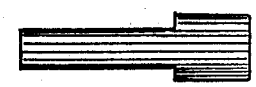

Depending upon the original shape of the pattern cut in the carbon fiber/polymer sheet, the resulting cylinder can be various shapes. For example, if a triangular pattern is cut (FIG. 12), the resultant cylinder (FIG. 13) will be tapered at both ends. If a stepped pattern is cut (FIG. 14), a cylinder with stepped cross-sectional diameters (FIG. 15) will result.

With this process, a curved composite structure can result if a suitable mold is used that has a curved mold surface.

Figure 16:
FIGS. 16–19 are schematic views showing the sequence of steps in making an implant.
Figure 17:
Figure 18:
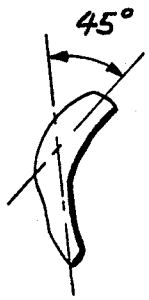
Figure 19:

Using this process to produce a hip implant, for example, which comprises a tapered stem which curved to a neck which is at an angle of 45° from the stem, the following procedures may be followed:

1. From a carbon fiber/polysulfone sheet, cut a pattern of the shape in FIG. 16;
2. Roll the pattern into a cylinder as shown in FIG. 17;
3. Mold under approximately 1000 psi pressure and 650° F. for 45 minutes using a curved mold that replicates the desired hip implant design (FIG. 18); and
4. Fix a spherical metallic head to the neck geometry using a suitable adhesive (FIG. 19) (an epoxy or molten polysulfone may be used).

With this process as described, fiber orientation will be uniaxial and will follow the curvature of the prosthesis.

By cutting the original pattern out of the carbon fiber/polysulfone sheet so that the fibers are off axis of the sheet by 10° for example, the resultant cylinder will contain fibers that spiral at 10° off axis, thus providing a three-dimensional fiber array to the structure. Such fiber orientation will improve torsional and shear strengths of the structure when compared to uniaxial fiber orientation.

In forming the cylinder, as an alternative to cutting an original pattern from the carbon fiber polysulfone sheets so that the fibers are off axis, one can also wrap the sheet at a bias to fiber orientation to achieve the same result. However, an additional trimming step will be required in this variation. Additionally, one can use two or more separate sheets in forming the cylindrical block wherein the axis of orientation is varied from one sheet to the next to adjust the modulus values. Once the cylindrical form is obtained, it can easily be molded to the desired final shape. By employing the additional sheets in forming the cylinder, one can further tailor the tensile and modulus properties of the device along its longitudinal axis to meet the specific functional requirements of the device.

In the two processes described, the final shape can be achieved by either machining, or in relatively simple shapes by molding to the finished shape.

A third method of achieving a final prosthesis shape is as follows:
1. Construct the structural member of the implant in the general finished shape by one of the methods described above;
2. Either by compression or injection molding, overmold the structure of number 1 with a suitable polymer, such as polysulfone, or with a molding compound consisting of short segments of carbon fiber in a matrix of polysulfone;
3. The mold for this overmolding step can be the exact shape of the finished prosthesis.

EXAMPLES

A test series was conducted to evaluate the difference in response of living bone to the implantation of hip prosthesis of identical design, but with some being fabricated from a standard orthopedic metal, cast Co-Cr-Mo alloy, and some being fabricated from a lower modulus carbon fiber reinforced polysulfone composite. Canines were used as the test model. The composite prosthesis was fabricated by the method first described in the above test. Two-dimensional plys of carbon fiber/polysulfone composite sheets were stacked into a block mold with alternate plys containing fibers oriented at +15° and −15° to the axis of the block. After blocks of this type were molded, finished canine hip implants were machined from the blocks. The flexural bending strength and flexural modulus of elasticity of this ±15° composite, determined by three-point bending tests were 90 ksi and 9 msi, respectively. Comparative tensile strength and modulus values of the cast Co-Cr-Mo alloy are reported to be 80 ksi and 32 msi, respectively.

At one implant per animal, several composite and Co-Cr-Mo devices were implanted and will be retrieved from the animals at incremental periods of up to 2 years. In addition to functional performance, at sacrifice, the implant and surrounding tissue is to be examined histologically, and periodic radiological examination (x-ray) is performed.

At 6 weeks after implantation, differences in the bone tissue adjacent to the implants were seen. Dramatic new bone growth could be seen macro and microhistologically in the calcar region and the region of the femur adjacent to the tip of the implant stem of the animals with composite implants. This bone growth was also demonstrated radiographically at 6 weeks and 12 weeks post implantation. Alternatively, at 6 weeks post implantation of the Co-Cr-Mo implant, regions of bone resorption were seen histologically in the calcar region and the region of the femur adjacent to the tip of the implant stem. Radiologically, a radiolucent zone could be detected in areas around to Co-Cr-Mo implants as early as 12 weeks post implantation, suggesting the initiation of implant microloosening.

In this invention, two methods of fabricating composite material implants are presented. Variations to these two methods are also possible. Instead of using uniplanar sheets of carbon fiber in a polysulfone matrix, a weave of carbon fiber coated with polymer may be used. These weaves typically contain continuous carbon fibers at two different angle orientations, usually at 90° to one another. Other variations of similar scope could also fall within the bounds of this invention.

What is claimed is:

1. In a femoral stem suitable for permanent human implantation into the natural femur, the femoral stem including an elongate shaft extending in an axial direction and having a size and shape for implantation within the medullary canal of the natural femur, and a neck suitable for replacement of the natural femoral neck, the neck being unitary with the shaft and extending from the shaft in a direction angled with respect to the axial direction of the shaft such that the axial direction and the angled direction define a plane to be aligned with the medial-lateral direction upon implant of the femoral stem, the improvement wherein the shaft and the neck are comprised of a number of first uniplanar layers of continuous unidirectional filament carbon fibers and a number of second uniplanar layers of continuous unidirectional filament carbon fibers, with the carbon fibers of each layer extending parallel to one another along a respective axis of orientation and being embedded in a respective matrix of non-biodegradable, bio-compatible thermoplastic polymer, the layers being in a stacked arrangement generally parallel to one another and essentially parallel to said plane, the axis of orientation of the fibers of the first layers being aligned essentially with the axial direction, the axis of orientation of the fibers of the second layers being offset from the axial direction up to ±90° relative to the axial direction, at least some first layers alternating with at least some second layers within the stacked arrangement, and wherein the number of first layers in the stacked arrangement of layers is greater than the number of second layers.

2. The invention of claim 1 wherein at least 60% of the stacked arrangement of layers are first layers, the balance of the stacked arrangement of layers being second layers.

3. The invention of claim 1 wherein 60% of the stacked arrangement of layers are first layers, 30% of the stacked arrangement of layers are second layers in which the axis of orientation of the fibers is offset ±15° from the axial direction, and 10% of the stacked arrangement of layers are second layers in which the axis of orientation of the fibers is offset ±90° from the axial direction.

4. The invention of claim 1 wherein 70% of the stacked arrangement of layers are first layers, and 30% of the stacked arrangement of layers are second layers in which the axis of orientation of the fibers is offset ±45° from the axial direction.

5. The invention of claim 1 wherein the polymer is present in the range of 30% to 70% by weight of the femoral stem.

6. In a femoral stem suitable for permanent human implantation into the natural femur, the femoral stem including an elongate shaft extending in an axial direction and having a size and shape for implantation within the medullary canal of the natural femur, and a neck suitable for replacement of the natural femoral neck, the neck being unitary with the shaft and extending from the shaft in a direction angled with respect to the axial direction of the shaft such that the axial direction and the angled direction fine a plane to be aligned with the medial-lateral direction upon implant of the femoral stem, the improvement wherein the shaft and the neck are comprised of at least one sheet of continuous unidirectional filament carbon fibers embedded in a matrix of non-biodegradable, bio-compatible thermoplastic polymer and extending generally parallel to one another along an axis of orientation, the being rolled upon itself into a spiral configuration about the axial direction to form the femoral stem.

7. The invention of claim 6 wherein the axis of orientation of the fibers is parallel to the axial direction.

8. The invention of claim 6 wherein the axis of orientation of the fibers is offset relative to the axial direction such that the fibers extend in a helical spiral configuration.

9. The invention of claim 6 including a plurality of sheets of continuous unidirectional filament carbon fibers embedded in a matrix of non-biodegradable, bio-compatible thermoplastic polymer, the fibers of each sheet extending generally parallel to one another along an axis of orientation, the sheets being rolled upon themselves into a spiral configuration about the axial direction to form the femoral stem.

10. The invention of claim 9 wherein the axis of orientation of the fibers of at least one of the sheets is parallel to the axial direction.

11. The invention of claim 6 wherein the axis of orientation of the fibers of at least one sheets is offset relative to the axial direction such that the fibers of that layer extend in a helical spiral configuration.

* * * * *